United States Patent [19]

Zlotnik et al.

[11] Patent Number: 5,431,885
[45] Date of Patent: Jul. 11, 1995

[54] CARTRIDGE FOR DEODORIZING, DISINFECTING OR HUMIDIFYING APPARATUS AND ARTICLE FOR CARTRIDGE

[76] Inventors: Clifford B. Zlotnik, 4717 Lougean Rd., Pittsburgh, Pa. 15207; Arnold H. Zlotnik, 1000 Sullivan Dr., West Homestead, Pa. 15120

[21] Appl. No.: 827,081

[22] Filed: Jan. 23, 1992

[51] Int. Cl.⁶ ............................................. A61L 9/04
[52] U.S. Cl. .................................... 422/122; 422/5; 422/123; 422/124; 239/60
[58] Field of Search .................. 422/5, 122, 123, 124; 239/60

[56] References Cited

U.S. PATENT DOCUMENTS

| | | |
|---|---|---|
| 2,614,820 | 10/1952 | Boydjieff ........................... 422/124 |
| 3,990,848 | 11/1976 | Corris . |
| 3,990,855 | 11/1976 | Cort . |
| 4,035,451 | 7/1977 | Tringali . |
| 4,059,422 | 11/1977 | Steiner ................................ 422/124 |
| 4,271,092 | 6/1981 | Sullivan . |
| 4,276,236 | 6/1981 | Sullivan . |
| 4,452,500 | 6/1984 | Zlotnik . |
| 4,579,717 | 4/1986 | Gymlay . |
| 4,647,428 | 3/1987 | Gymlay . |
| 4,743,406 | 5/1988 | Steiner et al. . |
| 4,931,224 | 6/1990 | Holzner, Sr. ....................... 422/124 |
| 4,931,258 | 6/1990 | Zlotnik et al. . |
| 4,968,456 | 11/1990 | Muderlak et al. .................. 422/124 |

Primary Examiner—Timothy M. McMahon
Attorney, Agent, or Firm—Hymen Diamond

[57] ABSTRACT

A cartridge including a cylindrical annulus of a porous material adapted to be impregnated with vaporizable deodorizing, disinfecting or humidifying material, having a plurality of openings encircling its central opening, a container having at one end a base having a plurality of openings therein open at the opposite end with this opening bounded by a seat for the annulus, and a battery extending between the base and the open end encircled and partially supported by the boundary of the central opening in the annulus. The cartridge does not have a battery where used for apparatus which already has a power supply.

14 Claims, 4 Drawing Sheets

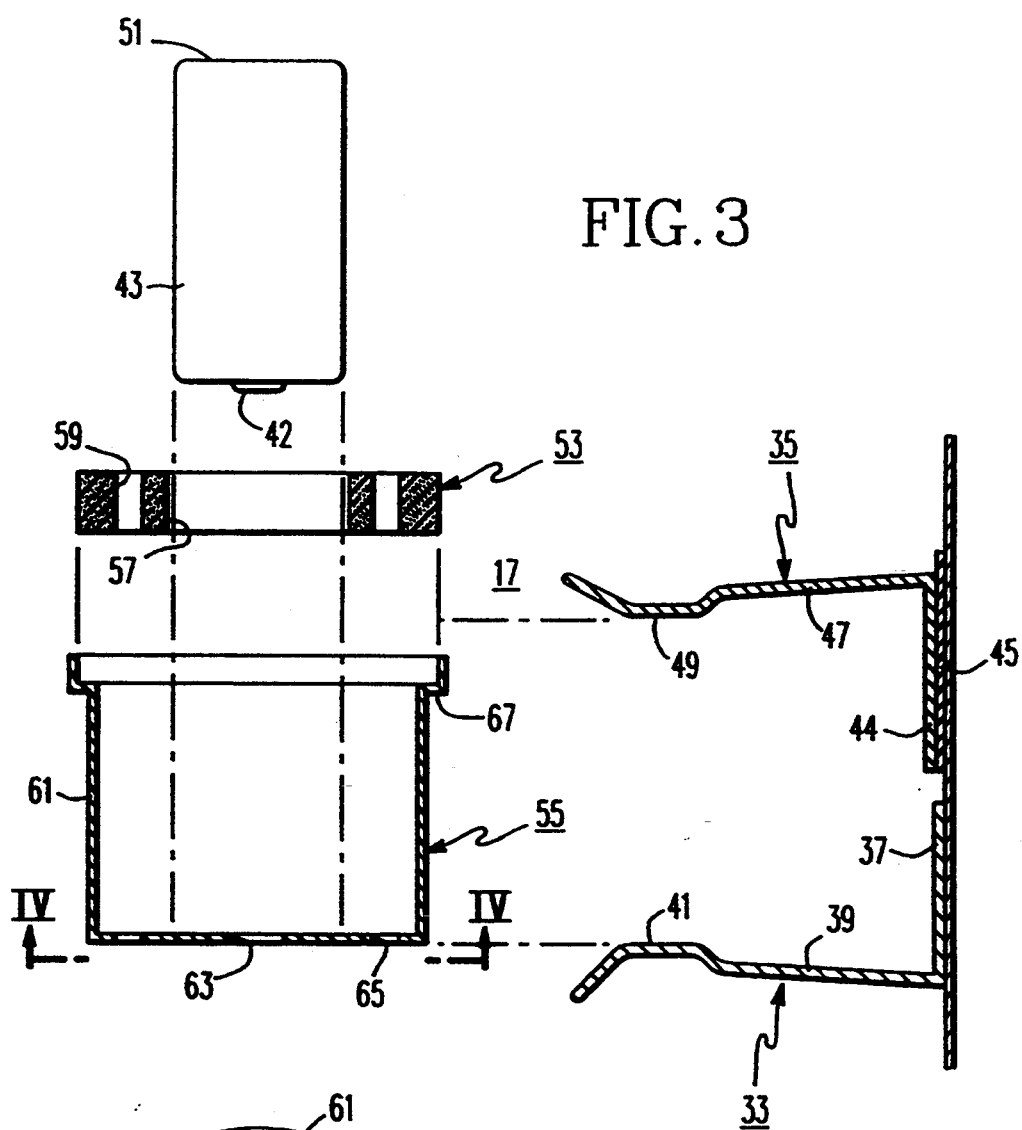
FIG. 3
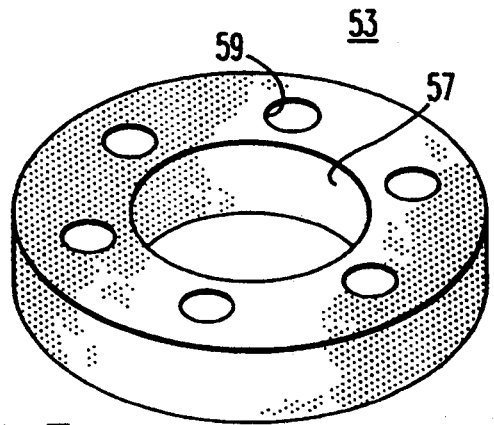
FIG. 4
FIG. 5

CARTRIDGE FOR DEODORIZING, DISINFECTING OR HUMIDIFYING APPARATUS AND ARTICLE FOR CARTRIDGE

BACKGROUND OF THE INVENTION

This invention relates to the art of diffusing a vaporizable material in a region for air freshening the region and, specifically, for deodorizing, disinfecting or humidifying the region or for other like purposes. The diffusion is affected by an air stream produced by a fan usually driven by a battery. The vaporizable material and the battery are spent at intervals, typically of a month or less and require replacement and this invention has particular relationship to the replacement of this battery and/or material. This invention is disclosed herein as applied to deodorizing, disinfecting or humidifying. This invention is also adaptable to slime, fungus or mildew control by dispersing a liquid or a soluble solid in the medium to be controlled. It is understood that the adaptation of the principles of this invention to other purposes than those disclosed here is within the scope of patentable equivalents of this application or of any patent issuing on or as a result of this application.

U.S. Pat. No. 4,743,406, Steiner-Bajek, is typical of the prior art relating to this invention. Steiner discloses a cartridge 40 (FIG. 3) for an air freshener. The cartridge has a double-walled container, inner wall 46 (FIG. 6) and outer wall 48. A battery 32 is disposed in the well defined by the inner wall and the vaporizable, deodorizing material 37 in the annulus defined between the inner and outer walls. Other prior-art cartridges are similarly structured. The prior-art cartridge disclosed by Steiner and others has the disadvantage that it requires the relatively costly double-walled container and the assembly of this cartridge or replacement of the deodorizing material is complicated and time consuming.

It is an object of this invention to overcome the disadvantages of the prior-art cartridges and to provide a replacable cartridge of simple and low-cost structure lending itself readily to assembly or replacement of parts for deodorizing, disinfecting or humidifying or other like purposes. It is also an object of this invention to provide such a cartridge for apparatus for deodorizing, disinfecting or humidifying, which apparatus has a power supply so that the cartridge does not require a battery. It is also an object of this invention to provide a readily replacable source of vaporizable material of simple structure for use in the replacable cartridge. It is an ancillary object of this invention to provide for controlling the generation of slime, fungus or mildew in a liquid medium by dispersing a liquid controlling agent in the medium.

SUMMARY OF THE INVENTION

This invention arises from the discovery that a block, typically an annulus or disk, of porous material impregnated with a vaporizable deodorant, disinfectant, or humidifier, when subject to the air stream produced by a motor-driven fan, releases adequate quantities of the vaporizable material to achieve the desired purpose of treating the air in a selected region. Marked improvement in the release or emission of the vaporizable material is achieved by providing the block with holes or openings, thus enhancing the surface from which the release takes place. Typically, the porous block may be composed of a mixture of a binder with plaster of Paris and terra cotta material, moistened and mixed in a powder ribbon blender to a paste. The paste is then formed in a die and heated in a kiln to harden. This porous block can be procured from pottery manufacturers. A spent block may be reimpregnated or a new block impregnated by immersing the block in a liquid vaporizable material, particularly under light pressure. Blocks of other components, typically such as light density polyethylene or light density polypropylene are within the scope of equivalents of this invention.

In accordance with this invention, there is provided a cartridge for deodorizing, disinfecting or humidifying apparatus which includes a porous block and a container or can. The block has a central opening encircled by a plurality of openings, displaced radially from the central opening. The container has a base which also has a central opening encircled by a plurality of openings and is open opposite the base. This opening is bounded by means for supporting the block, typically a seat for the block. The seat is dimensioned so that the block is a slip-fit in the seat and is readily removable. A battery extends between the central openings in the block and base and is a loose-fit in the block so that batteries of different diameter can be positioned in the cartridge. The poles of the battery are accessible through the central opening in the block and the central opening in the base. A spent block or a spent battery can be readily replaced.

The container is molded from a plastic material, typically heavy duty polyethylene or polypropylene, and is of low cost so that, if desired, the whole cartridge may be discarded and replaced when the block and battery are spent.

In use, the cartridge is mounted in the deodorizing, disinfecting or humidifying apparatus with the motor terminals of the apparatus in firm electrical contact with the poles of the battery and with a porous impregnated block and the base aligned so that the air stream driven by the fan passes through the holes in the block and base. The flowing air spreads over the surface of the block, releasing the vaporizable material from the surface of the block and the surfaces of the openings into the region whose air is being treated. The battery and the remainder of the cartridge are supported by the motor terminals.

Also, in accordance with this invention, there is provided a cartridge for use with apparatus which has a power supply, either a battery or public utility supply. This cartridge includes a container having a perforated base and a perforated porous block. The base has a seat in which the block is a slip-fit. The block and base while perforated do not require provisions for a battery. This cartridge is mounted in the deodorizing, disinfecting or humidifying apparatus with the block and base, aligned with the air stream from the apparatus so that the air stream passes over the block and through the openings in the block and the base and releases vaporizable material from the block.

In accordance with another aspect of this invention, there is provided a porous block impregnated with a leachable material, typically orthophenyl phenol, for counteracting slime, fungus or mildew or the like or a perfume for counteracting disagreeable odor. The block is seated in a container which is provided with openings for the flow of the liquid. The liquid to be treated flows through and out of the container contacting the block and leaching the OPP or the like or the perfume.

BRIEF DESCRIPTION OF THE DRAWINGS

For a better understanding of this invention, both as to its organization and as to its method of operation, together with additional objects and advantages thereof, reference is made to the following description taken in connection with the accompanying drawings, in which:

FIG. 3 is an exploded view in longitudinal section of a cartridge in accordance with this invention for apparatus, sans its own a power supply;

FIG. 4 is a plan bottom view taken in the direction IV—IV of FIG. 3;

FIG. 5 is a view in isometric of a block in accordance with this invention which is impregnated with a vaporizable deodorant, disinfectant or humidifier in the practice of this invention;

DETAILED DESCRIPTION OF EMBODIMENTS

Figure 1:
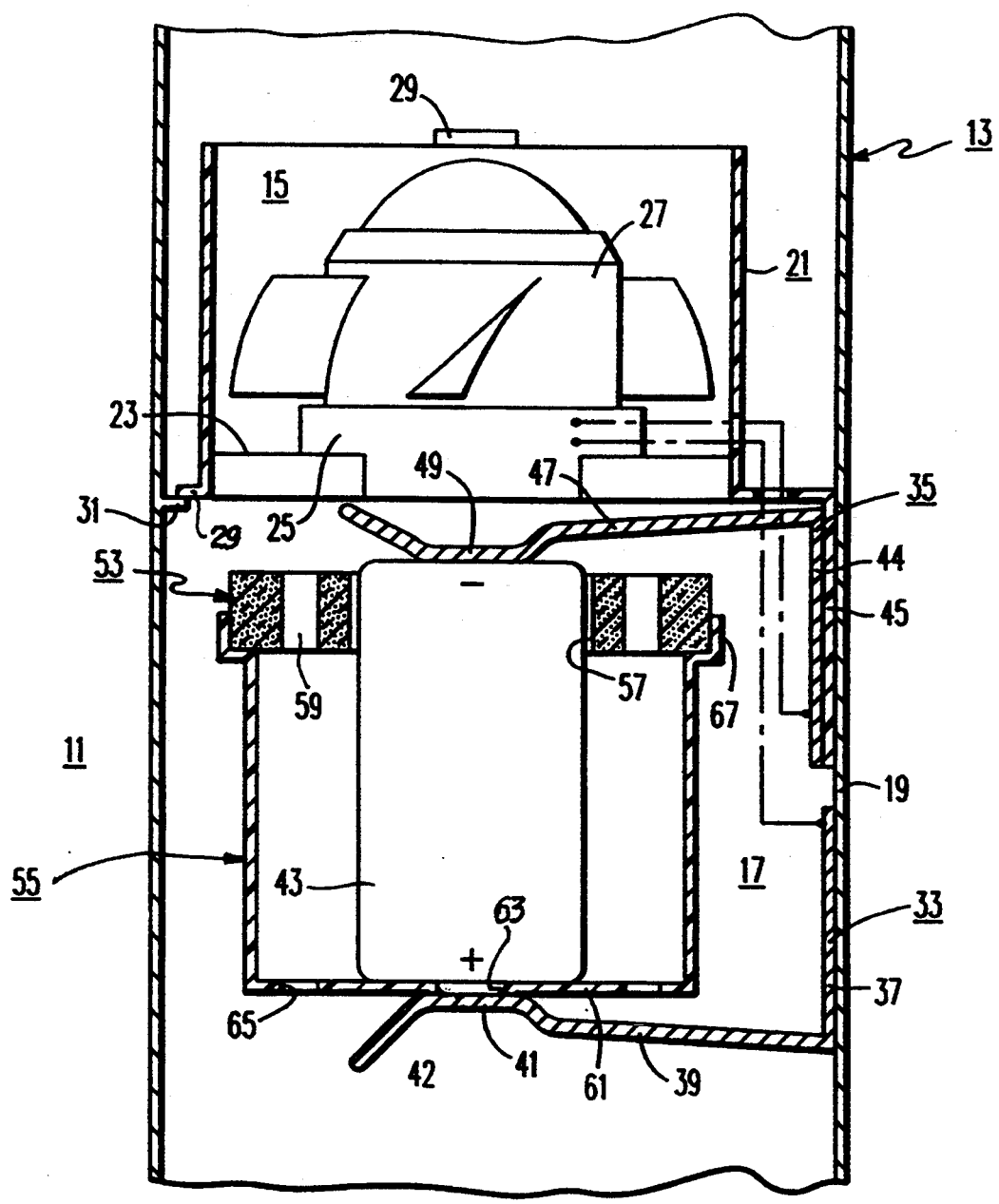
FIG. 1 is a view in longitudinal section of deodorizing, disinfecting or humidifying apparatus, sans its own power supply, including a cartridge in accordance with this invention.

FIG. 1 shows deodorizing, disinfecting or humidifying apparatus 11 including a bracket 13 in which is mounted an air-stream generating assembly 15 and a replacable cartridge 17 in accordance with this invention for energizing assembly 15 and for releasing the vaporizable material to deodorize, disinfect or humidify. The bracket 13 may be generally similar to Steiner's closure section 50 (FIG. 2), and may latch diagonally to a mounting section (not shown), such as Steiner's section 10. The bracket 13 includes an outer open container 19 in which the air-stream generating assembly 15 and the cartridge 17 are mounted.

The air-stream generating assembly includes a shell 21, typically of plastic, having internally extending spokes 23 which support a unit including a motor 25 and a fan or blower 27. The shell 21 is supported from the bracket 13 by oppositely disposed projections 29 which engage a lip 31 extending inwardly from the bracket. Battery terminals 33 and 35 are suspended from the bracket 13. The terminals 33 and 35 are composed typically of spring steel or other like alloy. Each terminal is of angular shape, the angle between them being somewhat less than 90°. One arm 37 of the terminal 33 is secured to the bracket 13, grounded to the bracket. The other arm 39 carries a projection 41 for connection to a pole of 42 of the battery 43 of the cartridge 17. An arm 44 of terminal 35 is secured to an insulating strip 45 which is, in turn, secured to the bracket 13. The other arm 47 carries a projection 49 for connection to the opposite pole 51 (FIG. 3) of the battery 43.

The cartridge 17 (FIGS. 1, 3) includes, in addition to the battery 43, a porous block 53 which in use is impregnated with a vaporizable deodorant, disinfectant or humidifier or the like and a container or can 55. The block 53 (FIG. 5) is typically of circularly annular shape but, within the scope of this invention, may be of other shapes, for example, in the shape of a rectangular parallelepiped. The block 53 has a central opening 57 adapted to accommodate the adjacent end of the battery 43. As shown in FIG. 1, the battery is positioned loosely in the opening so that batteries of different diameter may be accommodated. The block also has a plurality of openings 59 which extend around the central opening 57. The surfaces of the openings 57 and 59 materially enhance the total surface of the block through which the vaporizable material is released. The container 55 is of circularly-cylindrical shape and has a base 61 and is open at the top. The container 55 may be composed of plastic, typically heavy-duty polyethylene or polypropylene, by molding. The base 61 has a central opening 63 (FIG. 4) dimensioned to accommodate the pole 42 of the battery 43 and a plurality of openings 65 encircling the central opening. The open end of the container 55 is bounded by a ledge 67 which serves as a seat for the block 53. The ledge 67 is dimensioned so that the block is a slip-fit in the seat. The thickness of the block 53 substantially exceeds the axial length of the ledge 678 so that a substantial part of the block extends above the ledge, enhancing the release of vaporizable material. The ledge 67 should be of such axial length that the ledge effectively grips the block when the cartridge 17 is assembled.

In the use of cartridge 17, the block 53 is seated in seat 67 of the container 55. The battery is inserted in this subassembly with pole 42 extending into opening 63, with its end surface extending slightly outwardly and with its opposite end extending into opening 57 with its end surface extending slightly outwardly, thus completing the cartridge 17. The cartridge is locked in the deodorizing, disinfecting or humidifying apparatus 11 between the terminals 33 and 35 or analogous terminals of like apparatus. The terminals 33 and 35 are composed of metal of such thickness that the projections 41 and 49 exert substantial force across the battery to hold the cartridge firmly. The hole 63 is dimensioned with reference to pole 42 and the seat 67 with reference to the diameter of the battery 43, that the battery and block 53 are firmly gripped and when mounted in the apparatus 11, the cartridge 17 is physically and mechanically stable.

In the use of the assembled apparatus 11, the motor 25 (FIG. 1) is energized by the battery 43, driving the fan 27. A stream of air is produced with which the openings 57 and 59 in the block 53 and the openings 65 in the container 55 are aligned. The stream spreads over block 53 and into its openings 57 and 59 and releases the vaporizable material with which block 53 is impregnated and carries it into the region whose air is to be treated through louvers (not shown) in the bracket 13.

Figure 2:
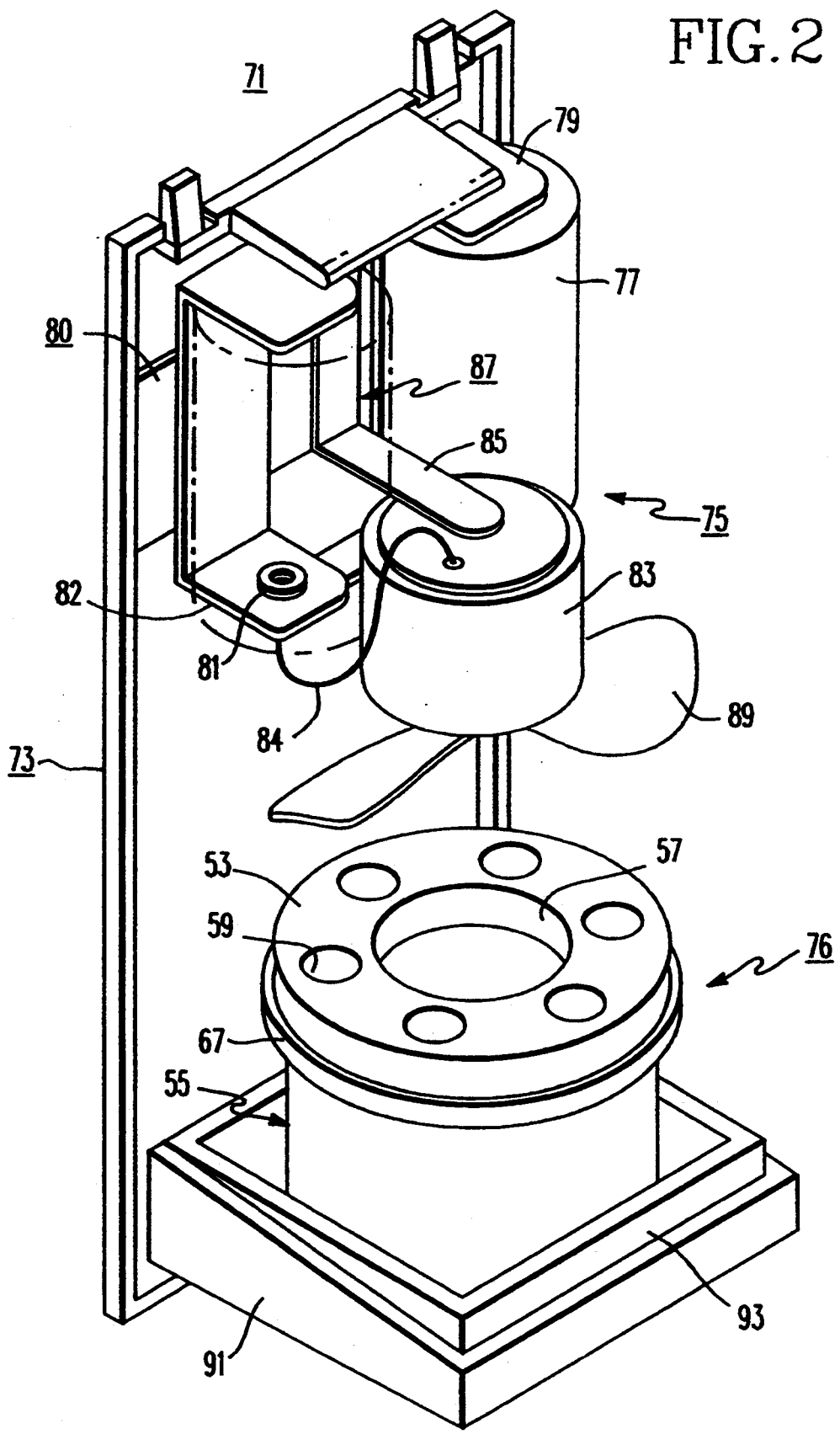
FIG. 2 is a view in isometric of deodorizing, disinfecting or humidifying apparatus with its own power supply and with a cartridge in accordance with this invention adapted for use in such apparatus.

FIG. 2 is deodorizing, disinfecting or humidifying apparatus including a frame 73, typically similar to the frame 3 of U.S. Pat. No. 4,931,258, Zlotnik et al. This apparatus includes an air-stream producing assembly 75 and a cartridge. The air-stream producing assembly 75 includes a battery 77 held firmly by terminals 79 and 81, connected to the poles of the battery. Terminals 79 constitutes one flange of a channel-shaped bracket 80. The other flange 82 carries the terminal 81 which is insulated from the flange. There are two brackets 80 suspended from the frame 73, both capable of receiving a battery. A conductor 84 connects the terminal 81 to the motor 83. The other terminal 79 grounds the pole of the battery to which it is connected to the brackets, to which the ground terminal (not shown) of the motor is also grounded. There is also a motor 83 supported cantilever-like from an arm 85 of an angle 87 suspended from the frame 73. A fan 89 is connected to the motor shaft (not shown) to be driven by the motor to produce a stream of air.

Figure 6:
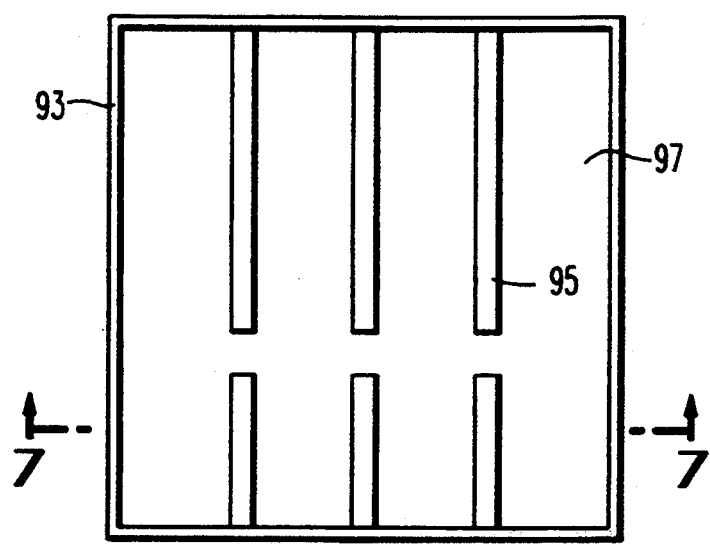
FIG. 6 is a plan view of the tray of the apparatus shown in FIG. 2 in which the cartridge, according to this invention, is positioned.
Figure 7:
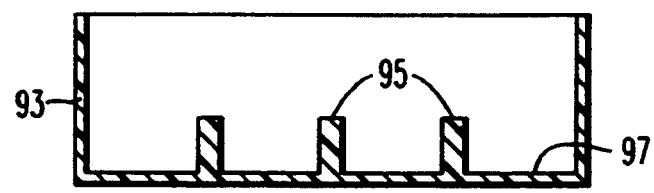
FIG. 7 is a view in section taken along line VII—VII of FIG. 6.

The frame 73 has a shelf 91 which is aligned centrally, coaxially with the motor shaft. On the shelf 91, there is a tray 93 (FIGS. 2, 6). A plurality of bars 95 project from the base 97 of the tray 93. The cartridge 76 is supported on bars 95 on the base 97 of the tray 93. Typically, the cartridge may consist of the porous block 53 and the container 55 of the cartridge 17 of the apparatus 11 shown in FIG. 1. Such a cartridge is used in the interest of economy, the components of the cartridge may have widely different shapes and structures. As in the cartridge 17, the block 53 is seated in the ledge 67 of the container 55.

In the use of the apparatus, the air stream generated by the air-stream producing assembly 75 envelops the block 53 and passes through holes 57 and 59 of the block 53 and through the holes 63 and 65 of the base 61 of the container 55. Then it passes under the container and the region between the bars 95 and out through louvers in the housing (not shown, 1 FIG. 1 Zlotnik). The air carries with it the vaporizable material released from the block 53.

Figure 8:
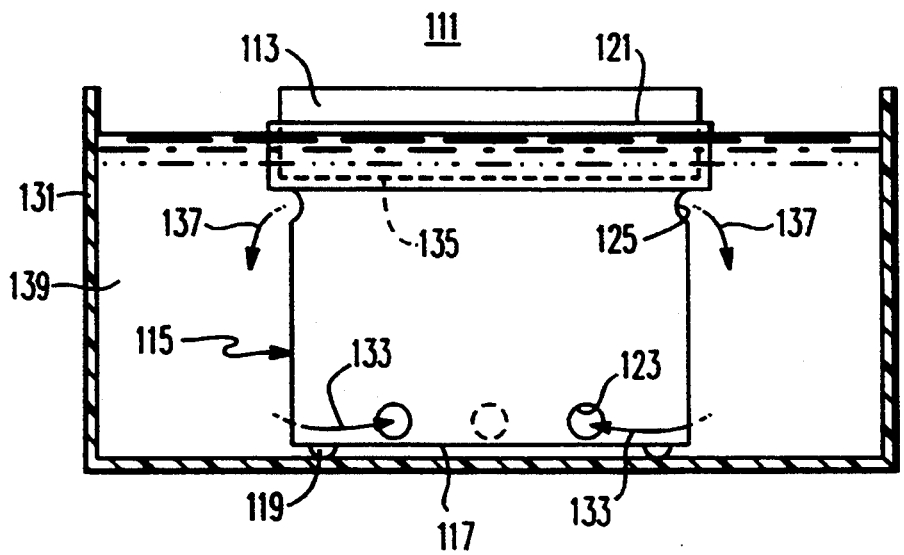
FIG. 8 is a diagrammatic view for apparatus in accordance with this invention and for practicing the method of this invention for slime, fungus or mildew control.

The apparatus shown in FIG. 8 includes a cartridge 111 having a porous block 113, typically of circularly-cylindrical shape, and a container or can 115, typically in the shape of a hollow circular cylinder. The container 115 has a solid base 117 from which legs 119 extend. The container 115 is open at the top and has a ledge 121 which serves as a seat for the block. The ledge 121 has a depth such that the block 113 extends to a substantial extent into the container 115. Openings 123 and 125 are provided above the base 117 of the container and just below the ledge 121.

In use, the porous block 113 is impregnated with a treating chemical, for example, orthophenyl phenol in the case of control of slime, fungus or mildew or a perfume in the case where an odor is to be counteracted, for example, in an ink-bath of a printing press where xylene is in use. The cartridge is disposed in the medium to be treated, for example, in the drop pan 131 of an air conditioner. As the liquid rises in the drip pan 131, it enters the holes 123, as indicated by the arrows 133, and rises in the container 115 to a level 135 above the holes 125. The liquid flows out of the holes 125 as indicated by the arrows 137 back into the pool 139, thus circulating through container 115. At the level 135, the liquid bathes the block 113, reacting with and releasing the orthophenyl phenol, which reacts to reduce or suppress the slime, fungus or mildew.

While preferred embodiments of this invention have been described herein, many modifications thereof are feasible. This invention is not to be restricted except insofar as is necessitated by the spirit of the prior art.

We claim:

1. A replacable cartridge for use with deodorizing, disinfecting or humidifying apparatus, said apparatus having blower means for producing a stream of air, said blower means having means adapted to mount and be energized by a replacable cartridge; said replacable cartridge including: a generally cylindrical container having a base at one end and an opening at the opposite end, said opening being defined by a ledge extending around said opening, a substantially noncompressible, nonconsumable porous solid annulus having a main opening seated in said ledge with its surface facing said base space from said base, said annulus being adapted to be impregnated with a vaporizable deodorizing, disinfecting or humidifying material and said cartridge also having a battery for energizing said blower means extending between said base and said annulus and through the main opening in said annulus, said battery being encircled in supporting relationship by the surface of said annulus defining said opening and said base, said cartridge having means, adapted to cooperate with said mounting and energizing means to mount said cartridge in energizing relations with said blower means with said battery in energizing relationship with said blower means, and said annulus and base aligned with said blower means to transmit said stream of air to release the impregnating vaporizable material as a deodorizing, disinfecting or humidifying vapor.

2. The cartridge of claim 1 wherein the annulus and the battery are mutually separably mounted in the container so that they may be separately removed and replaced.

3. The cartridge of claim 1 wherein the annulus includes auxiliary openings in addition to the main opening into which the battery extends, said auxiliary openings encircling said main opening, and wherein the base includes at-least-one opening, said auxiliary openings and said at-least-one opening being adapted to be aligned by the mounting means to transmit said stream of air through said annulus when said cartridge is aligned with the blower, said auxiliary openings enhancing the impregnation of the annulus with vaporizable material and the release of vapor from said annulus by increasing the surface of said annulus which is impregnable and from which vapor is released.

4. A replacable cartridge for use with deodorizing, disinfecting or humidifying apparatus, said apparatus including a fan and a power supply connected to said fan for driving said fan and also including means adapted to receive a replacable cartridge; said replacable cartridge including: a substantially noncompressible, nonconsumable, solid annulus of porous material adapted to be impregnated with a vaporizable deodorizing, disinfecting or humidifying material, said annulus having at-least-one generally axially extending opening, and a container having a base at one end having at-least-one opening therein and having an opening at the opposite end, said last-named opening having means for receiving said annulus, said cartridge being adapted to be positioned in said receiving means of said apparatus with the openings in said annulus and base aligned with said fan so as to transmit the current air generated by said fan when energized.

5. The cartridge of claim 4 wherein the annulus has, in addition to the at-least-one axially extending opening, a plurality of auxiliary openings around the periphery of said at-least-one opening to enhance the impregnation of the vaporizable material in and the emission of said vaporizable material from said annulus.

6. The replacable cartridge of claim 4 wherein the receiving means is dimensioned with respect to the annulus so that said annulus is readily removably positioned in said receiving means.

7. A replacable cartridge for use with deodorizing, disinfecting or humidifying apparatus, said apparatus including means for producing a stream of air, and means adapted to mount said replacable cartridge in said apparatus; the said replacable cartridge including: a substantially noncompressible, nonconsumable block of porous material adapted to be impregnated with a vaporizable deodorizing, disinfecting or humidifying material, said block having at-least-one opening transverse to its surface therein, and said replacable cartridge also including a container, said container having at one end a base having at-least-one opening therein and having an opening at the opposite end, said last-name opening being bounded by a seat adapted to seat said block with its surface facing said base spaced form said base, said mounting means being adapted to mount said replacable cartridge in said apparatus with said opening in said block and said opening in said base generally aligned to pass said stream of air.

8. A replacable cartridge for use with deodorizing, disinfecting or humidifying apparatus, said apparatus having a fan when energized for producing a stream of air and also having means adapted to mount said replacable cartridge in said apparatus; said cartridge including: a substantially noncompressible, nonconsumable block of porous material having a generally central opening therein and also having a plurality of openings encircling said central opening, said porous material being adapted to be impregnated with a vaporizable deodorizing, disinfecting or humidifying material, said replacable cartridge also including a container having at one end a base having a plurality of openings therein and being open at the opposite end with the open end being bounded by means for supporting said block with its surface facing said base spaced from said base, and said replacable cartridge also including a battery extending from said base and passing through said central opening in said block and being engaged by the boundary of said central opening; said mounting means being adapted to mount said replacable cartridge with said battery in energizing relationship with said fan and said encircling openings in said block and said openings in said base aligned to pass said stream of air.

9. In combination in deodorizing, disinfecting or humidifying apparatus having means for producing a stream of air; a replacable cartridge including:
(a) a substantially noncompressible, nonconsumable, porous block having a generally axial, generally central opening therein, said block being adapted to be impregnated with a deodorizing, disinfecting or humidifying material,
(b) a container having a perforated base and having an opening opposite said base,
(c) seating means connected to said container for said block bounding said opening on which said block is seated with its surface opposite said base spaced from said base, said block extending above said seating means, and
(d) a battery disposed on said base and extending through the opening in said block contiguous to the inner surface of said block but movable with respect to said contiguous surface; said apparatus including means, connected to said airstream producing means, adapted to mount said replacable cartridge in said apparatus with said porous block and said base generally aligned in the stream produced by said airstream-producing means, whereby said airstream passes over and through said block and through said base releasing as vapor from the vaporizable material impregnated in said block.

10. The combination of claim 9 wherein one of the opposite poles of the battery is at the end of the battery extending through the porous block and the other of the opposite poles is the end engaging the base and wherein the mounting means includes electrical conductors, connected to the airstream-producing means in current-conducting relationship therewith and one of said electrical conductors engages said one opposite pole of said battery and another electrical conductor engages said base and said other pole of said battery, whereby said electrical conductors both mount said cartridge and connect said stream-producing means to be energized by said battery.

11. The combination in deodorizing, disinfecting or humidifying apparatus having means for producing a stream of air, and power-supply means connected to said airstream-producing means for energizing said airstream-producing means; a replacable cartridge including:
(a) a substantially noncompressible, nonconsumable, porous block having a generally axial, generally central opening therein, said block being adapted to be impregnated with a deodorizing, disinfecting or humidifying material,
(b) a container having a perforated base and having an opening opposite said base, and
(c) seating means connected to said container for said block bounding said opening on which said block is seated; said apparatus including means connected to said airstream-producing means for mounting said replacable cartridge with said block and said base aligned in the path of the airstream produced by said airstream-producing means, whereby said airstream passes over and through said block and through said base releasing as vapor the vaporizable material with which said block is impregnated.

12. The combination of claim 11 wherein the mounting means includes a tray on which the container is mounted, said tray including means spacing the base of said container from the bottom of said tray providing an outlet for the airstream which passes through the block and base of the container.

13. An article of manufactured for use in deodorizing, disinfecting, or humidifying apparatus comprising a substantially noncompressible, nonconsumable, porous block having a plurality of openings therein, generally perpendicular to its surface; said block being composed of porous material and being adapted to be impregnated with a vaporizable deodorizing, disinfecting or humidifying material, said openings having bounding surfaces such as to enhance the surface through which said block is impregnated with vaporizable material and from which said vaporizable material is vaporized.

14. The article of claim 13 wherein the block is an annulus having a central opening and a plurality of surface enhancing openings encircling said central opening.

* * * * *